United States Patent [19]

Rohde

[11] Patent Number: 4,694,271

[45] Date of Patent: Sep. 15, 1987

[54] DEVICE FOR STABILIZING MAGNETIC ZONES

[76] Inventor: Bruno Rohde, Blindenhaselbach 6, 8267 Neumarkt-St. Veit, Fed. Rep. of Germany

[21] Appl. No.: 850,675

[22] Filed: Apr. 11, 1986

[30] Foreign Application Priority Data

Apr. 13, 1985 [DE] Fed. Rep. of Germany ....... 3513281

[51] Int. Cl.⁴ .............................................. H01F 7/02
[52] U.S. Cl. ..................................... 335/302; 335/306
[58] Field of Search ................ 335/302, 303, 304, 306

[56] References Cited

U.S. PATENT DOCUMENTS 4,222,021  9/1980  Bunker ............................. 335/303 X
4,382,245  5/1983  Harrigan ............................. 335/306

FOREIGN PATENT DOCUMENTS 961725  6/1964  United Kingdom ................ 335/303

Primary Examiner—George Harris
Attorney, Agent, or Firm—Brady, O'Boyle & Gates

[57] ABSTRACT

The invention concerns a device in cube (1) or cuboid shape (3) exhibiting on each side (4) centrally arranged magnets (2, 5), the magnets projecting outwardly always with the same pole. They serve for eliminating damaging effects of magnetic zones of the earth surface for man, animals, and plants.

4 Claims, 2 Drawing Figures

DEVICE FOR STABILIZING MAGNETIC ZONES

The invention relates to a device for stabilizing the magnetic zones which move and, respectively, oscillate and rotate in the vertical, horizontal, and diagonal directions.

It is known that ground radiation can exert an adverse influence on man and animal, plants and trees. Involved herein are rising and falling magnetic fields of the global grid systems, differing in polarity. The most closely knit network encompassing the entire globe is named after Hartmann. The further grid system, extending diagonally to the Hartmann network with respect to compass points, and likewise surrounding the entire globe is named after Curry. Also underground water streams generate ground radiation on account of friction. This radiation exhibits the property of generating around itself an oscillating, vertical, horizontal and diagonal magnetic field.

The invention is based on the object of aiding man, in particular, in avoiding at his resting and sleeping place the effects of this radiation which are unfavorable to him. In this context, it should also be noted that numerous types of trees, plants, animals and insects as well require this radiation to sustain life.

An effort is disclosed hereinbelow how to eliminate the effect of the magnetic zones moving and, respectively, oscillating and rotating in the vertical, horizontal, and diagonal directions.

A disk-shaped or rod-like permanent magnet is placed on the ground where a Hartmann or Curry grid network has been found. Depending on which one of the two poles of the magnet points to the ground, the field now is either enhanced or no longer measurable at all. If the field has become stronger, then a further permanent magnet is to be mounted in antipole fashion thereabove, at a spacing at which the magnets no longer exert too great a mutual influence. If then both magnets are furthermore turned outwards with their north poles, so that they are now arranged vertically exactly in one direction and in exact superposition, then this arrangement of the magnets will arrest any polarity of any grid network in its flux. When placed exactly over the underground stream, this arrangement also will bring this oscillating field to a standstill. When placing this arrangement into the horizontal, then it brakes horizontal oscillations in one direction, namely the one facing the arrangement.

In case horizontal oscillations emanate from a direction shifted by 90°, and these oscillations are to be braked, then this aforementioned arrangement is to be rotated by 90°. In the cube form, all of these effects are present at all times, even if the horizontal anti-poles are rotated by 45° with respect to the horizontal oscillation zones—this being the most unfavorable instance for horizontal oscillations. The only condition posed is that the cube must always be disposed or mounted so that it is horizontal. If it is displaced more than 25° from the horizontal position, it loses a great portion of its effectiveness.

Fields of any desired length and size can be surrounded with a long series of cubes on which are mounted continuous magnet bars respectively in the center along the four long sides, pointing always with the same pole toward the outside, and the same effect can be attained as with the cube.

Differently strong magnetic eddies are produced, depending on speed and friction, in transport vehicles on land, sea and in the air. Persons show different reactions to this phenomenon. Nausea and aggressiveness are merely two of the best known consequences. It can also be assumed that there is a correlation between frequency of accidents and these magnetic eddies.

The invention also overcomes these magnetic eddies in transportation conveyances. Depending on the size and number of cubes or cube series in the form of cuboids, mounted at suitable locations in the conveyance, the magnetic field is brought to a standstill, and deleterious eddies are prevented.

The mode of operation of this invention can be proved by means of a dowsing rod, a pendulum, and other measuring instruments known for this purpose.

The efficacy and endurance of the cube or cuboid depend on the quality and longevity of the magnets. If the effect is to be fully successful, then the correct site must be found for the cube. More expensive, but safer, on the other hand, is enclosing the desired locations with the long cuboids if done by an unskilled person. If the aforementioned system is displaced, or even happens to come among children's toys, it cannot do any damage. It is just as harmless as any other magnet.

The drawing illustrates a cube according to this invention and, respectively, a cuboid of approximately natural size.

Figure 1:
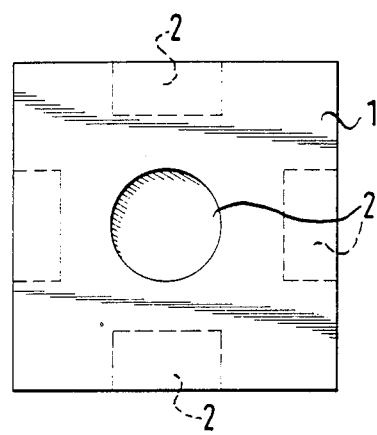
FIG. 1 is a cube according to the present invention.
Figure 2:
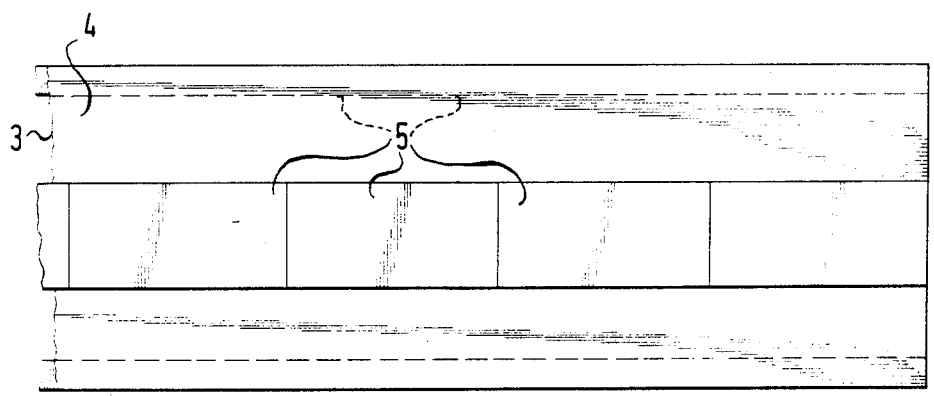
FIG. 2 is a combination of a plurality of cubes in the shape of a cuboid, likewise effective in accordance with the invention.

The cube 1 which consists of wood, for example, exhibits in the center of each side respectively one magnetic disk 2. According to FIG. 2, the cubes are combined into a cuboid 3 exhibiting along its longitudinal sides 4 centrally arranged magnetic bars 5.

I claim:

1. A device for stabilizing magnetic zones by means of magnets, comprising a cube of non-magnetic material, a separate magnet connected in the middle of each side of said cube whereby the magnets on each side of the cube are separated from each other, the magnets being in the form of plates having flat surfaces positioned perpendicular to the direction of a magnetic zone, each of said magnets having a single polarity on each side and all outwardly facing flat surfaces of all of the magnets being of the same polarity, and the magnets on opposite sides of said cube being spaced from each other a distance such that the magnetic influence on each other is just avoided.

2. A device as set forth in claim 1, including a plurality of said cubes positioned in surrounding relation to a given area to form a closed circuit around the given area.

3. A device as set forth in claim 1, in which said magnets in the form of plates are disk-shaped.

4. A device as set forth in claim 1, in which said magnets in the form of plates are rectangular-shaped.

* * * * *